US008006542B2

(12) United States Patent
Jones, Jr.

(10) Patent No.: US 8,006,542 B2
(45) Date of Patent: Aug. 30, 2011

(54) METHOD FOR CONTAMINANT DETECTION USING AN ODOR MARKER

(76) Inventor: Arthur T. Jones, Jr., Albuquerque, NM (US)

( * ) Notice: Subject to any disclaimer, the term of this patent is extended or adjusted under 35 U.S.C. 154(b) by 1910 days.

(21) Appl. No.: 11/026,373

(22) Filed: Dec. 29, 2004

(65) Prior Publication Data

US 2010/0297602 A1 Nov. 25, 2010

(51) Int. Cl.
*G01N 7/00* (2006.01)

(52) U.S. Cl. ...................................................... 73/31.03

(58) Field of Classification Search .................. 73/23.2, 73/31.03

See application file for complete search history.

(56) References Cited

U.S. PATENT DOCUMENTS 4,563,893 A 1/1986 Tanyolac et al.
4,896,547 A 1/1990 Arney et al.
5,675,070 A 10/1997 Gelperin
5,915,268 A * 6/1999 Linker et al. .................. 73/23.2
6,073,499 A * 6/2000 Settles ....................... 73/864.81
6,386,015 B1 5/2002 Rader et al.
6,610,977 B2 * 8/2003 Megerle ........................ 250/287
6,613,571 B2 * 9/2003 Cordery et al. ................. 436/48
7,755,494 B2 7/2010 Melker et al.

OTHER PUBLICATIONS

U.S. Appl. No. 12/772,583, filed Sep. 16, 2010, Melker, Richard J.
U.S. Appl. No. 12/599,743, filed Oct. 21, 2010, Melker, Richard J.
U.S. Appl. No. 12/064,673, filed Oct. 7, 2010, Melker, Richard J.
Beate Giffo-Schmitt; International Preliminary Report On Patentability; Jul. 3, 2007; Wipo, Switzerland.

* cited by examiner

*Primary Examiner* — Hezron Williams
*Assistant Examiner* — Nathaniel Kolb
(74) *Attorney, Agent, or Firm* — David McEwing

(57) ABSTRACT

The present invention is a method and apparatus for contaminant detection of body parts, such as hands, and or their coverings, such as clean room suits or gloves, and small objects. Particularly, the method and apparatus involve collecting air samples containing aerosolized contaminate particles from the objects and analyzing the sample for presence of a contaminate. Aerosol lab-on-a-chip and/or electronic nose devices are utilized for the detection of contaminant particles.

3 Claims, 9 Drawing Sheets

FIG. 4
PRIOR ART

SECTION A-A

METHOD FOR CONTAMINANT DETECTION USING AN ODOR MARKER

FIELD OF THE INVENTION

The present invention involves detection of contaminants such as bacteria, viruses, and body fluids. More particularly, it detects such contaminants in nano- to micro-scale, most typically in sanitation apparatus or sanitation monitoring apparatus such as but not limited to independent units, units combined with hand dryers or clean room detectors.

BRIEF DESCRIPTION OF THE DRAWINGS

FIG. 4 is a box diagram of an aerosol lab-on-a-chip device;

SUMMARY OF THE INVENTION

Figure 1:
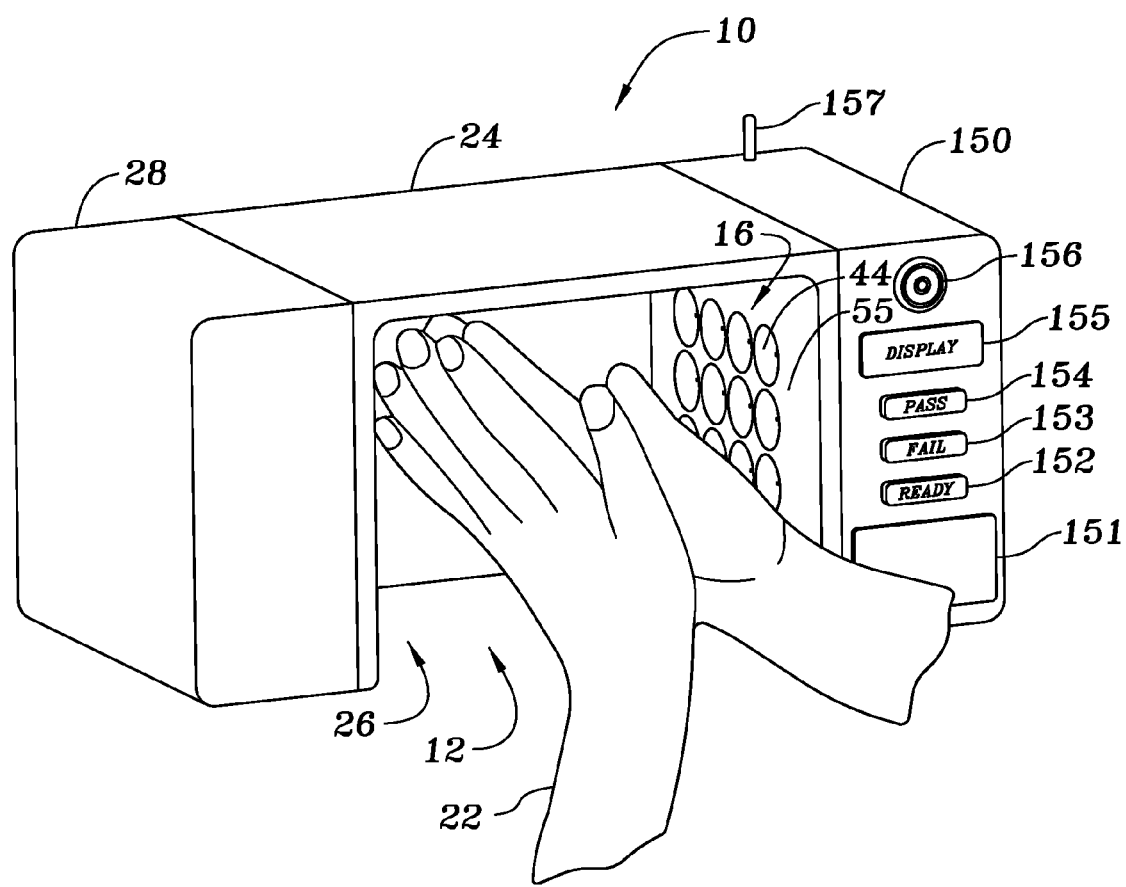
FIG. 1 depicts a fixed embodiment of the apparatus of the invention, showing placement of the object for analysis, here hands, in the detection area of the invention and the relation to the collection area.

The present invention is a method and apparatus for contaminant detection to ensure cleanliness and/or that sanitary procedures have been undertaken and were successful. Particularly, the method and apparatus involve collecting air samples containing aerosolized contaminate particles from an object and analyzing the sample for presence of a contaminate. Aerosol lab-on-a-chip and/or electronic nose devices are utilized for the detection of contaminant particles.

More particularly, the invention includes a method for detecting contamination of objects (including but not limited to body parts, whole bodies, utensils, clothing such as gloves, gowns, masks, shoes, foot covers, clean suits, etc.) including providing an object; collecting air surrounding the object; and analyzing the collected air by utilizing an ALOC detector to determine the presence of contaminated particles. Additional steps may include creating airflow across the object before collecting the air; utilizing an odor marker, utilizing an odor within a known object as an odor marker. The method may have additional steps of providing exchangeable objects having known odor markers and maintaining a database or record of the analysis of the odor markers to indicate use of particular exchangeable objects, for example, using gloves with different odor markers and requiring use of certain gloves at certain times of day to ensure gloves are changed frequently. The contaminant may be selected from the group consisting of bacteria, viruses, protozoans, blood, body fluids, tissues, chemicals, and dirt.

The invention also includes an apparatus having a collector unit and an ALOC detector unit in fluid connection with the collector unit for detecting the presence of contaminants on objects. The apparatus may also have a telemetry unit in electrical connection with the detector unit, a controller unit in electrical connection with the detector unit, and/or a controller unit in electrical connection with a telemetry unit.

The collector unit has a collecting surface with at least one air inlet, and can have at least one funnel-type device surrounding the at least one air inlet. It may also have an air handling unit disposed to create air flow across an object and into the collector. The air handling unit may have at least one air nozzle disposed within a cavity of an object, and may be electronically controlled by a controlling unit.

The apparatus may be a portable unit. Additionally, it may have an odor marking unit. Alternately, the detector unit may comprise an electronic nose device.

BACKGROUND OF THE INVENTION

In a time when we now understand more clearly the causes and effects of disease, we have at our disposal the means with which to avoid many sources of infection: the use of sanitary methods, especially hand washing. Unfortunately, most people simply don't perform the task as well or as often as needed. The main problem is that germs are too small to see. People can't simply wash off visible dirt and expect their hands to be "clean". Additionally, people, for whatever reason, do not spend the adequate amount of time necessary to properly clean their hands.

Experts agree that effective hand washing requires both soap and water. (Merely rinsing one's hands with water alone will not suffice.) The hands must be wet thoroughly and lathered with soap. Then the individual must rub the soapy water all over the hands and fingers for at least twenty (20) to thirty (30) seconds, including underneath the fingernails, and then rinse thoroughly to ensure proper sanitation has occurred. Unfortunately, people simply don't do this. "*Want to Help Fight Disease? Just Wash Your Hands*." www.yourskinandsun.com/article1039.html (Aug. 18, 2003).

While businesses such as restaurants and hospitals frequently install signs in restrooms to remind their employees that they "must" wash their hands before returning to work, there has never been an effective way for an employer or other supervisor to monitor if this hand washing did, in fact, occur (unless sinks are installed in the work area and heavily monitored). Further, even if an employee has washed their hands, there has never been a way to ensure that the hands are satisfactorily clean, or if substandard sanitary practices have occurred. The problem is not limited to businesses or institutions alone. Every day parents, guardians, and care givers everywhere lament children's hand washing practices. Further, these selfsame care givers have never had a way to ensure that their own hands, much less the children's hands, were properly washed as well. Given the virulence of bacteria and viruses emerging in the world scene now, it is becoming ever more important to ensure proper hand washing has occurred.

The Centers for Disease Control and Prevention (CDC) estimates that approximately 76 million people suffer from foodborne illnesses and 5,000 die from these illnesses in the United States each year. The CDC, in a review of contributing factors to foodborne disease outbreaks over a five year period, estimated that poor personal hygiene was a contributing factor in over a third of the outbreaks.

In a study reported in the Journal of Infectious Diseases in Children, fecal coliforms were detected on the hands of some twenty (20) percent of daycare staff evaluated. Further, a third of the facilities studied had poor hand washing systems and no policy for hand washing before eating or after playing outside. (Kendall, Pat, "*Hand Washing Important to Preventing Spread of Disease*", Colorado State University Cooperative Extension, www.ext.colostate.edu/pubs/columnnn/nn010320.html. (Mar. 20, 2001).) These are particularly worrisome numbers when the type of infectious diseases common to these child care facilities are considered.

Diseases with respiratory tract symptoms are often spread by airborne droplets or by surfaces contaminated with nose/throat discharges. The sneezing and coughing of an infected child can result in some of the germs becoming air-borne. In addition, sick children will often contaminate their hands and other objects with infectious nasal/throat discharges. Some of the infections passed in this way are the common cold, chickenpox, influenza, measles, meningitis (viral and bacterial), mumps, whooping cough (pertussis), rubella, streptococcal infection, and viral gastroenteritis. Intestinal tract infections are often spread through exposure to viruses, bacteria, or parasites in the feces and are transmitted by the fecal-oral route. This means that the germs leave the body of the infected person in the feces and enter the body of another person through the mouth. In most situations, this happens when objects that have become contaminated with undetectable amounts of feces are placed in the mouth. (Fecal-oral transmission can also occur when food or water is contaminated with undetectable amounts of human or animal feces.) Studies have shown that the sites most frequently contaminated with feces are hands, classroom floors, toilet flush handles, toys and tabletops. Germs spread in this way include: *Campylobacter* species, cryptosporidium, *E. coli* O157, *Giardia*, hepatitis A (infectious hepatitis), *Salmonella* species, *Shigella* species, and a variety of intestinal viruses. (Colorado Dept, of Public Health and Environment, "*Infectious Disease In Child Care Settings: Guidelines for Child Care Providers*" December 2002; www.cdphe.state.co.us/dc.epidemiology/ChildCareflipchart02a.pdf.)

Clearly, there is a grave health risk present when proper sanitary methods are not employed and diseases, not limited to those listed above, are spread. Physicians agree that the best way to prevent the spread of illness is washing the hands properly, but how can one be sure that hands have been washed properly, whether in a home, daycare, medical, industrial, commercial or other setting? The present art does not allow for real time testing of the hands or other small objects to check for contaminants. Therefore, there is a strong felt need in the art for an apparatus and method for real time testing of hands or other body parts for contaminants in order to avoid unnecessary transmission of such contaminants.

Further, this danger can be extended. Small items may also carry germs that can put one's health at risk. A dropped pacifier or a toy handled by another child can easily transmit germs to a healthy child. To carry the analogy to the business world, a spatula dropped in a restaurant can become contaminated with whatever germs the restaurant's employees have "walked in". (Germs are often carried on shoes.) Further, there are conceivable instances where the utmost care should be taken in disease or contaminant prevention: hospitals, in particular, operating rooms or intensive care units, and clean rooms for industry. These types of specialized environments require the highest level of cleanliness. Unfortunately, until now, the most relied on "check" for cleanliness has been the honor system—trusting workers to sufficiently scrub up.

The problems the honor system creates can be clearly seen in the CDS's own "*Guideline for Hand Hygiene in Heath-Care Settings: Recommendations of the Healthcare Infection Control Practice Advisory Committee and the HICPAC/SHEA/APIC/IDSA Hand Hygiene Task Force*", published at www.cdc/gov/mmwr/preview/mmwrhtml/rr5116a1.htm and at *MMWR Recommendations and Reports* 51 (RR16); 1-44 (Oct. 25, 2002). This guide sets forth the state of the art: that the performance indicator for hand washing is for health care facilities to periodically monitor and record adherence as the number of hand-hygiene episodes performed by personnel/number of hand hygiene opportunities and to provide feedback to the personnel. Therefore, the only feedback that could be given would be subjective based on the number of hand washings and, likely, the duration. There is no method or apparatus in use to actually check for contamination.

There is clearly a need in the art for actual contaminant detection capability to facilitate a quick, reliable answer to individuals in industry, healthcare, and on a personal basis of the presence of contaminants. Further, the process needs to be repeatably reliable. Additionally, it would be extremely desirable to avoid complicated processes such as plating specimens in order to detect contaminants. Clearly unusable in a home situation, such detection methods are so time consuming as to be non-useful in other situations (such as commercial or medical) as well. Furthermore, there is a need in the art for identification of individuals in industry or healthcare that have not adequately cleaned their hands in hand washing. Subjective monitoring is not sufficient and impractical for continued monitoring.

DESCRIPTION OF A PREFERRED EMBODIMENT

The present invention comprises a novel detection apparatus and method for detection of contaminants on hands, other body parts, clean suits, small objects and the like. More particularly, it involves use of a contaminant detector utilizing an aerosol lab-on-a-chip (ALOC) device or electronic nose device to chemically detect contaminants by sampling the surrounding air.

For the purposes of this disclosure the following definitions shall apply:

Aerosol lab-on-a-chip (ALOC) is a device which integrates one or more of a variety of aerosol collection, classification, concentration (enrichment), and characterization processes onto a single substrate or layered stack of substrates;

Contaminants are materials or organisms found on the item to be examined which are foreign (or present in unusually high number) to the object itself and may include, but are not limited to, chemicals, fecal material, dirt and other detritus, microbes, viruses, fungi and protozoa;

Electronic noses are devices which are used for automated detection and classification of odors, vapors and gases. They are comprised of a chemical sensing system and a pattern recognition system (artificial neural network).

Items to be examined are any items small enough to fit in the detection unit, typically, body parts, including but not limited to hands and feet, small objects (such as spatulas, pens, etc.), whole persons, including but not limited to clean suits, shoes, gloves, hairnets, or clean room booties examination.

The preferred embodiment of the invention comprises a contaminant detection apparatus. The detection method comprises providing an object for analysis, collecting aerosolized contaminant particles from air surrounding the object, and analyzing the air to detect the presence of contaminant. Optionally, the additional step of creating airflow across the object may be used before the collection step.

The contaminant detector of the invention comprises an aerosol collector in fluid connection with a detector. The detector may utilize an aerosol-lab-on-a-chip or an electronic nose device. The apparatus may additionally comprise a controller and/or telemetry devices in electrical and/or electronic connection with the detector. Optionally, the controller may be in electrical and/or electronic connection with an optional air handling unit which provides an air flow across the object which is to be evaluated. Further optionally, an odor marker may be utilized for detection which will alert the controller that an object is in place and/or that the object has engaged in the sanitation process (i.e., hand-, foot-, object-washing). Finally, the apparatus may additionally utilize drying devices known in the industry, and may additionally comprise monitoring devices, preferably including card reader technology, including but not limited to RF technology and bar code readers, to alert monitoring stations to non-compliant hands, objects, etc. by sending an electronic signal or maintaining an internal electronic database tracking the testing and results of particular individuals.

Figure 2:
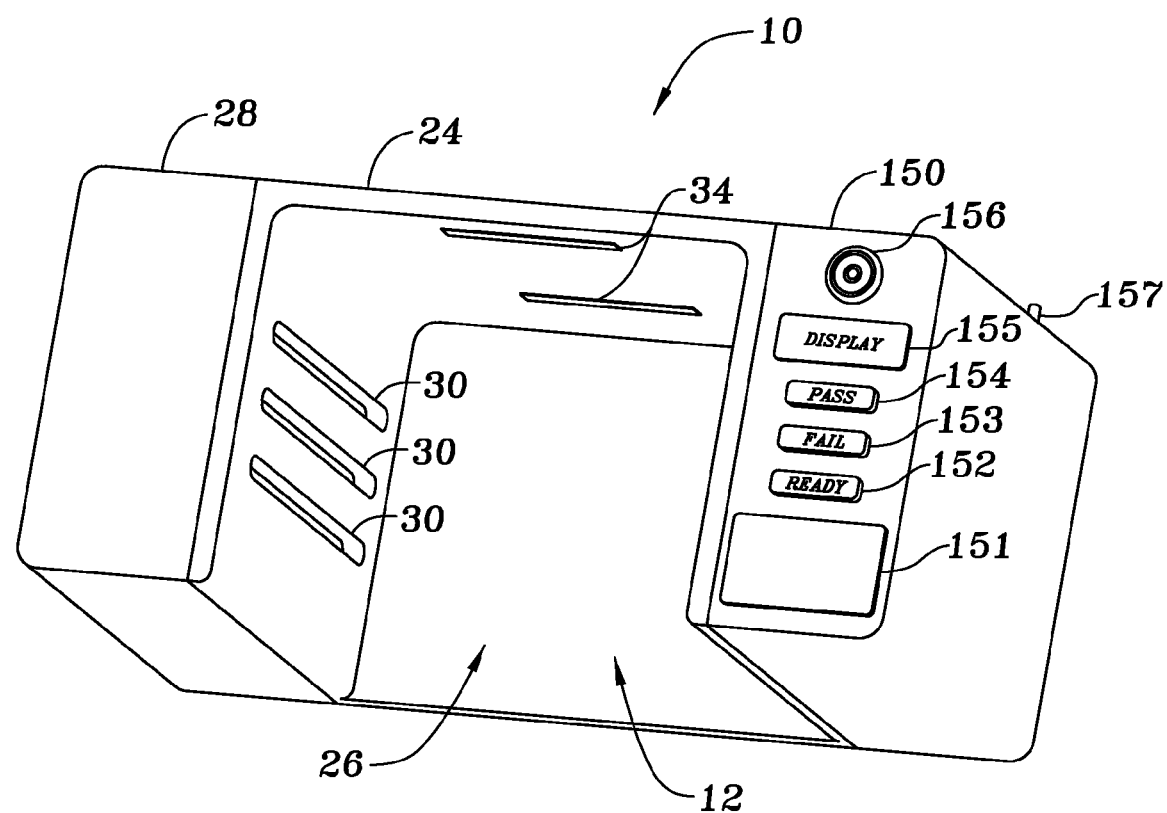
FIG. 2 is a perspective view of the embodiment of the apparatus as shown in FIG. 1, additionally depicting sensors and outlets of the air handler.
Figure 3:
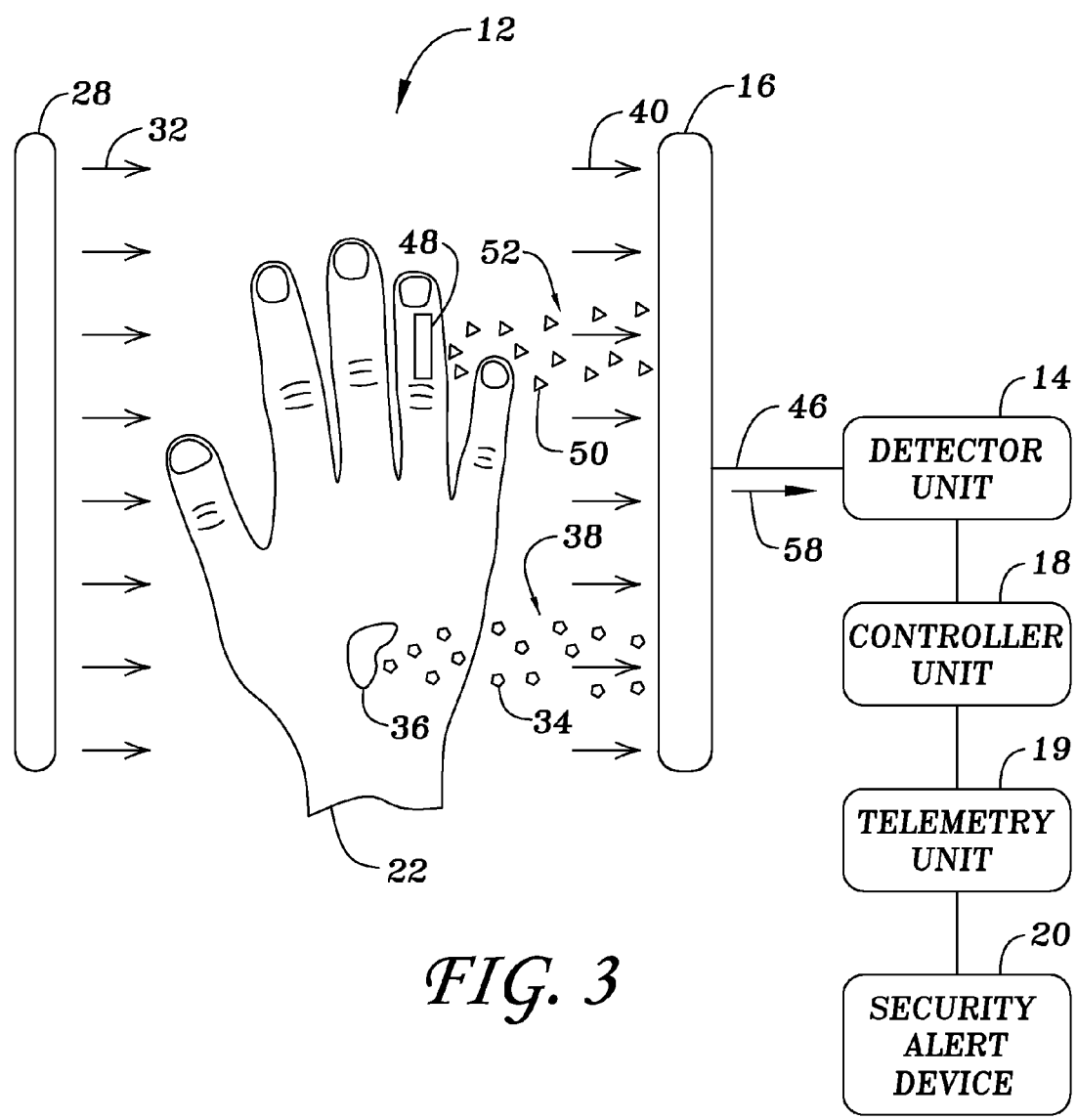
FIG. 3 depicts a generalized drawing of the apparatus/method of the invention, showing placement of a hand for analysis between an air handler and a collector, and the collection of aerosolized particles of contaminant and odor marker, and further showing a box diagram of the detector unit of the invention and optional controller, telemetry and security units of the invention.

The preferred contaminant detector apparatus 10 of the invention, as shown depicted in FIGS. 1-3, comprises detection area 12, aerosol collector 16, detection unit 14, and optional controller unit 18, optional telemetry unit 19, and optional security alert devices 20.

Object/objects for analysis 22, (which may include body parts, such as but not limited to hands and feet, whole bodies, gloves, masks, hats, hair nets, hair covers, clean room suits or booties, utensils, medical equipment, containers, and other objects sized for proximity to the detector) as shown in FIGS. 1, 3, 8, and 9, hands, are placed in somewhat close proximity with aerosol collector 16, preferably in an optional partially or wholly defined chamber created by forming opposing walls of a housing 24 of apparatus 10 to create one or more sides of chamber 26, allowing maximum beneficial airflow across hands 22. Preferably, the object is placed approximately fifteen feet or less from collector surface 55. More preferably, the object is placed approximately one foot or less from the collector surface, but not touching the collector surface (as this would contaminate the surface). Air flow handling apparatus 28, comprising a fan or other device for creating air movement known in the art may be optionally employed to create a sustained or varied air current 32 across object 22, utilizing one or more air outlets 30 opening into chamber 26 to allow air flow across object 22, or ambient air may be used. The air flow handler may optionally be electrically connected to an optional controller which can control the volume and/or speed of the air flow. Power for the air handler and/or the entire apparatus may be supplied by any means known in the art, typically electricity or, for portable units, batteries.

Figure 4:
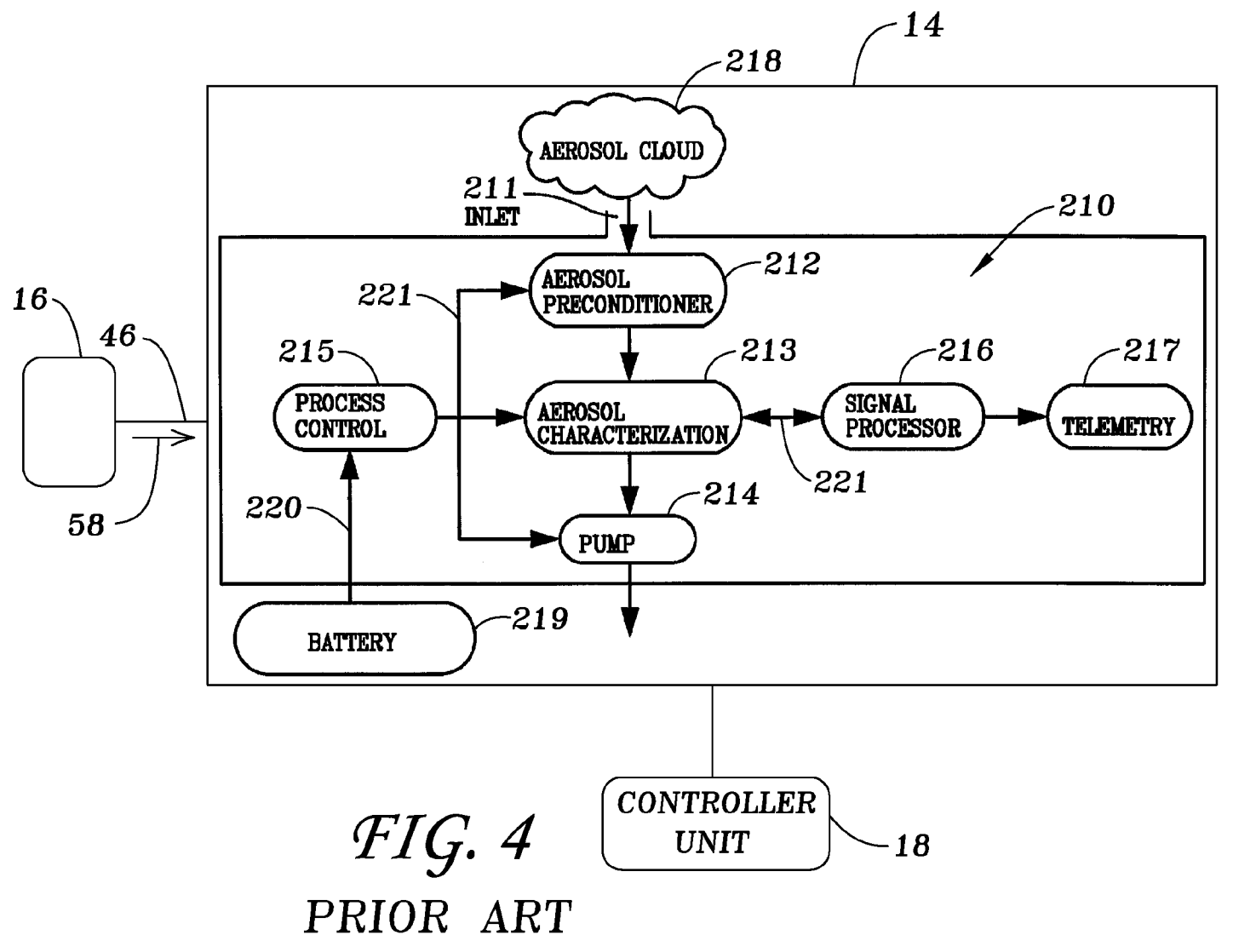

Naturally or mechanically aerosolized contaminant particles 34 arising from contaminant 36 on object 22 will be moved by air current or ambient air from object 22 and combined air current/aerosolized contaminant particles 38 will flow naturally (or in an assisted manner if forced air current 32 is applied) to aerosol collector 16 and into aerosol collector inlets 44. An assisted air flow is not required, but may be helpful in moving aerosolized contaminant particles or in providing the mechanical assist to aerosolize the particles from the surface of the object. Aerosol collector 16 is maintained in fluid (gaseous) connection with detector 14, preferably, by utilizing tubing 46 or other connective apparatus known in the art, disposed between collector 16 and detector 14, thereby allowing collected combined air flow/contaminant stream 58 to flow from collector 16 to detector 14. Detector 14 preferably comprises an aerosol lab-on-a-chip as described in U.S. Pat. No. 6,386,015 to Rader, et al. and as depicted in FIG. 4 and described herein. Detector 14 is preferably electrically connected to optional controller unit 18.

Detector 14 comprises an ALOC device as disclosed in Rader '015: a tool to collect, classify, concentrate, and/or characterize gas-borne particles. The basic principle underlying the ALOC is to take advantage of micro-machining capabilities to integrate a variety of aerosol collection, classification, concentration (enrichment), and characterization processes into a single package which is compact, rugged, self-contained, and inexpensive to manufacture. Thus, a suite of discrete laboratory aerosol characterization techniques could be combined onto a single substrate, or stack of substrates, along with aerosol preconditioners and gas handling processes. The ALOC is analogous to the integrated circuit, wherein a variety of discrete electronic (aerosol) components are combined onto a single chip to build-up complex electrical (aerosol characterization) systems. The performance of several of these analytic aerosol characterization techniques would benefit by miniaturization (e.g., particularly the inertial techniques). By constructing arrays of identical parallel modules, it should be possible to reduce gas velocities that could give a quadratic reduction in pressure drop and consequently a quadratic reduction in power consumption. As pointed out above, sampling discrepancies would also be reduced; i.e., by virtue of their close proximity on the chip, each technique could be analyzing essentially the same sample. The performance of preconditioners, such as concentrators or size sorters, would also benefit by miniaturization, and could be built into layers above the diagnostics as needed. Gas-moving devices, such as pumps or fans, can be provided external to or fabricated onto the ALOC to provide the gas throughput needed for the aerosol sampling and analysis but are optional not essential. Electronic circuitry could also be fabricated onto the ALOC to provide for process control (valves, switches, etc.), signal processing, data analysis, and telemetry. Moreover, if the ALOC can be made sufficiently small and rugged, it could be placed directly into harsh (corrosive, high temperature, etc.) environments.

A schematic of an embodiment of the ALOC is shown for a single aerosol characterization technique in FIG. 4. The device components in the flow path are formed on a substrate 210, and comprise an aerosol inlet 211, an aerosol condition (preconditioner) 212, an aerosol characterization module 213, and a gas moving means, or "pump", 214, necessary in the absence of a moving gas stream, to establish a gas flow through the aerosol characterization module(s) of sufficient volume and velocity to ensure that an adequate number of particles are sampled. Pump 214 may be provided external to substrate 210, or it may be fabricated onto substrate 210. Preconditioner 212 may or may not be needed depending on the application. Support components are also shown which provide an active process control 215, signal processing/data analysis (signal processor) 216, and telemetry 217. The aerosol inlet 211 is designed to receive gas-borne particles from an ambient aerosol cloud 218. Note that none, some, or all of the support components 215, 216, and 217 may be needed for a particular characterization technique. Any number of characterization modules (and support processes) may be combined in parallel or in series on a single-chip or stacked-chip ALOC; by combining characterization modules based on independent physical measurements, it would be possible to perform simultaneous analysis of a wide array of particle properties. In addition, construction of parallel arrays of identical devices (i.e., multiple copies of FIG. 4) on a single substrate would have the advantage of providing, increased overall device efficiency, signal enhancement, and in particular, increased operational flexibility. For example, an ALOC could be made to handle high total gas flow rates by assembling large numbers of individual devices operating at low flow rates (with lower pressure drops).

Finally, power for the device is provided by a standard low-voltage source, such as a battery 219, through a set of leads 220 connected to a data/power bus 221 located on the integrated chip. Power also may be supplied by a battery incorporated directly onto the ALOC substrate, or by any other means known to those skilled in the art.

The functions of the individual components are described briefly now. 1) The aerosol inlet must provide a path that admits the particle-laden gas into the ALOC assembly. The shape of the inlet must be designed carefully, as is well known in the prior art, so as to avoid particle inertial inlet losses and to provide a suitable gas inlet velocity profile, and to avoid large pressure drops. 2) The term aerosol condition is used hereinafter to describe any collection of processes that may be used to either classify, concentrate, or in some way manipulate an incoming stream of particles comprising an aerosol prior to those particles reaching a characterization module. As a classifier, the conditioner can be used to accept or reject particles above or below a desired size, or within a desired size range. As a concentrator, the conditioner can be used to preferentially increase the local concentration of particles in a desired size range. 3) The purpose of the aerosol characterization module is to provide a measurement of some physical property of the particle, including prior art such as techniques based on particle light including prior art such as techniques based on particle light scattering, inertial response, or electric mobility. Many of the in situ or extractive techniques discussed above would be suitable for miniaturization. A complete characterization of the aerosol would require a determination of the distribution of size, shape, and chemical, physical, and biological composition of the suspended particles comprising the aerosol. 4) A gas moving device may be necessary, in the absence of a moving gas stream, in order to establish a flow of a sufficient volume and velocity of gas, and therefore, an adequate number of particles, through the characterization module(s) in order to ensure an accurate measurement. The gas moving device can be any means capable of generating a pressure differential such as a mechanical pump, a sorp pump, a fan, or ion or diffusion pumps, and can be external to or fabricated onto the ALOC. 5) Active process control would include sensors, circuitry, and control devices on-board the ALOC that would collectively act to maintain critical process parameters within acceptable operating ranges. Lumped into this module are additional flow handling devices, such as channels and valves, which may be needed to distribute/direct the gas flow among the various characterization modules. 6) Circuitry could also be provided to allow on-board signal processing or data analysis that would be used to reduce raw physical measurements from the aerosol characterization module into useful form. As an example, a pulse-height analyzer could be used to determine the peak scattering intensity needed to size a particle based on its scattering profile while passing through an illumination source. Systems could also be envisioned that would collect single-particle data and reduce it to obtain size distribution functions. 7) Telemetry could be used to send the acquired data to a remote collection unit. 8) Power to the ALOC is supplied by a standard low-voltage source, such as by a battery, which could be either external to, or built onto, the ALOC substrate.

Alternately, the apparatus of the invention may utilize electronic nose technology as detector 14. The two main components of an electronic nose are the sensing system and the automated pattern recognition system. The sensing system can be an array of several different sensing elements (e.g., chemical sensors), where each element measures a different property of the sensed chemical, or it can be a single sensing device (e.g., spectrometer) that produces an array of measurements for each chemical, or it can be a combination. Each chemical vapor presented to the sensor array produces a signature or pattern characteristic of the vapor. By presenting many different chemicals to the sensor array, a database of signatures is built up. This database of labeled signatures is used to train the pattern recognition system. The goal of this training process is to configure the recognition system to produce unique classifications of each chemical so that an automated identification can be implemented.

The quantity and complexity of the data collected by sensors array can make conventional chemical analysis of data in an automated fashion difficult. One approach to chemical vapor identification is to build an array of sensors, where each sensor in the array is designed to respond to a specific chemical. With this approach, the number of unique sensors must be at least as great as the number of chemicals being monitored. It is both expensive and difficult to build highly selective chemical sensors.

Alternate embodiments of the apparatus of the invention may utilize natural air flows instead of or in addition to fans or pumps for directing aerosol particles into collector 16.

Further alternate embodiments would comprise portable units wherein an alternate power source known in the art (such as, but not limited to, batteries) would be utilized for the optional air handler 28, detector unit 14, optional controller unit 18, quality control devices as discussed below, optional telemetry devices 19 for the transmission of user and results information, and optional security devices 20 as discussed herein.

Quality control devices may be utilized to ensure that the air flow is sufficient and directionally oriented to detect contaminants. In particular, as shown in FIG. 3, odor markers 48 such as known chemicals sprayed or otherwise distributed onto the surface of object 22 can be utilized to determine sufficient detection, for example, identifying a particular chemical in a hand cleanser, germicides, or antibacterial solutions and designating the chemical as an "odor marker" and analyzing for the presence of the odor marker. One particularly useful method to ensure that employees change gloves or other similar items regularly would be to color code or otherwise mark gloves containing different odor markers for different times and requiring regular analysis in the inventive apparatus to detect the odor marker at the appropriate time. Aerosolized particles 50 of odor marker 48 may be carried by combined air flow/contaminate particle stream 40 to a collector 16. Collectors 16 may be placed in locations surrounding the object to collect particles 50 aerosolized and combined with air flow to form combined contaminant particle/and or odor market/air stream 40.

Additional control devices that may be assistive to a user could include optional display modules 152, 153, 154, 155, 156, for example, as shown in FIG. 2. Display module 152 depicts a light display to indicate when the apparatus is ready for use, a "ready light", display modules 153 and 154 alternately depict "pass" and "fail" indicators that would light up after analysis has occurred, depending on the result of the analysis. Additionally, or alternately, display module 155 depicts a display screen, such as an LCD screen, which could display instructions, and/or result readouts to a user. Also depicted is optional alarm module 156 which could provide, as with the other modules, a visual or aural signal to indicate that a contaminant has been detected and/or, optionally, that the unit 10 is contaminated. Obviously, other configurations of notification modules could easily be envisioned and utilized and are to be within the scope of the invention.

Further, the unit 10 may comprise a card reader or other ID sensor 151 which could identify a particular individual for either identification and/or record keeping purposes. Further, the unit may utilize remote technology, telemetry, such as RF technology to indicate to a monitor in a remote position what the analysis has indicated. Antenna 157, as shown in FIGS. 1 and 2, could be utilized to send wireless signals to a remote monitoring station or computer compiling a database of the results of the analyses provided by the detector to allow easy analysis/tracking of the sanitation practices of particular individuals or review of a group. Of course, the units may be wired for a traditional "hard wired" data transmission as well.

Figure 9:
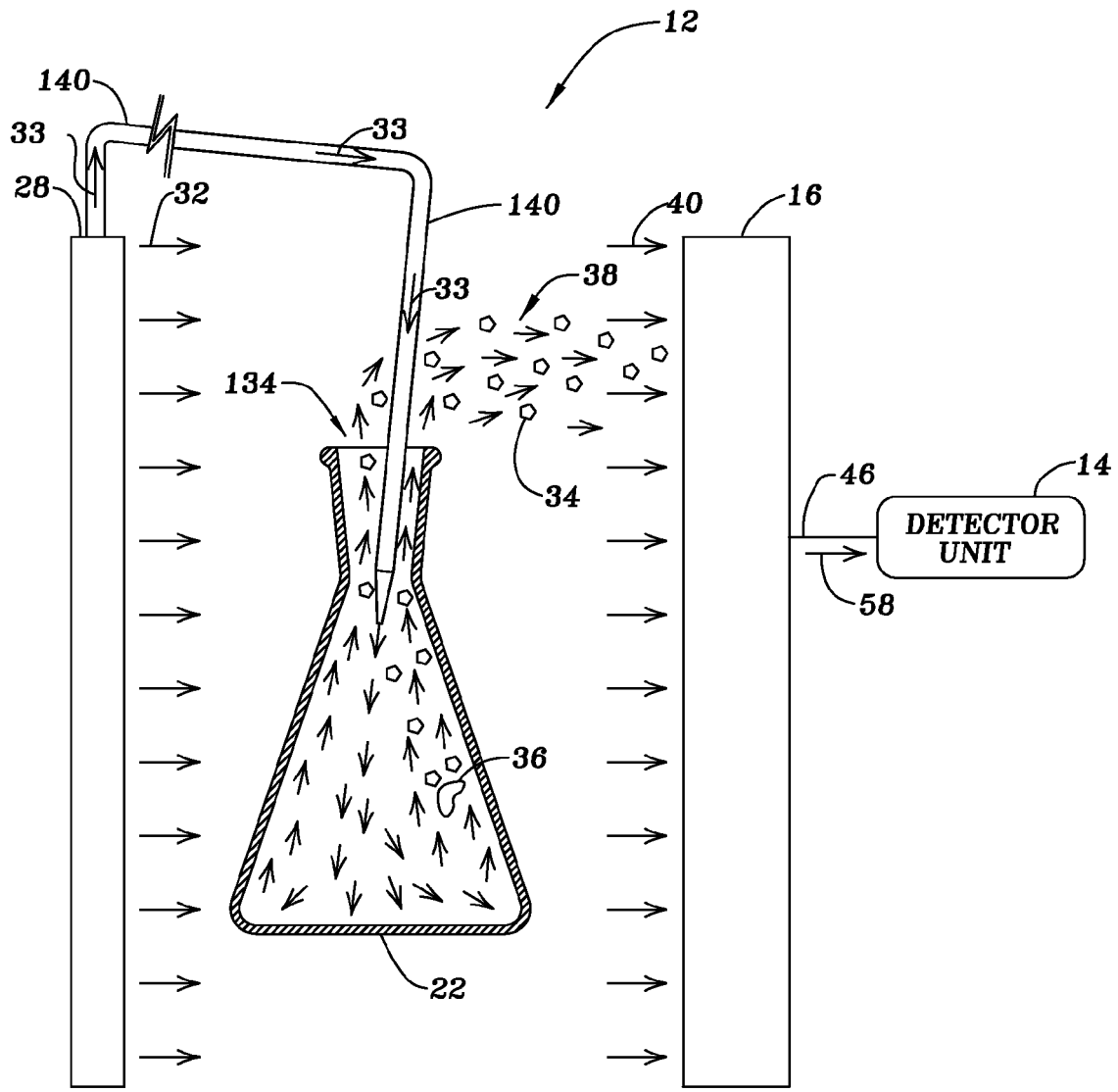
FIG. 9 depicts an air nozzle inserted into a cavity of an object to detect contaminates and shows external and internal examination of the object.

Further, in the case of some types of objects, it may be beneficial to provide an embodiment for detecting contaminants within a cavity area, for example, inside a container cavity. FIG. 9 depicts an embodiment of the invention wherein air nozzle 140 is placed within a cavity 134 of object 22. Air 33 flows from handler 28 through nozzle 140 and into cavity 134. Air stream 33 contacts a surface of cavity 134 and is diverted away from the surface. In this flow, air stream 33 combines with aerosolized contaminant particles 34 and or contaminant 36 to form combined contaminate particle/air stream 38. This combined particle/air stream 38 is then obtained by collector 16 for analysis. Meanwhile, preferably, (or at another time during the procedure), air flow 32 flows across an outer surface of object 22 (if an outer surface is desired to be analyzed for contaminants) to obtain aerosolized particulates for analysis by collector 16.

Figure 5:
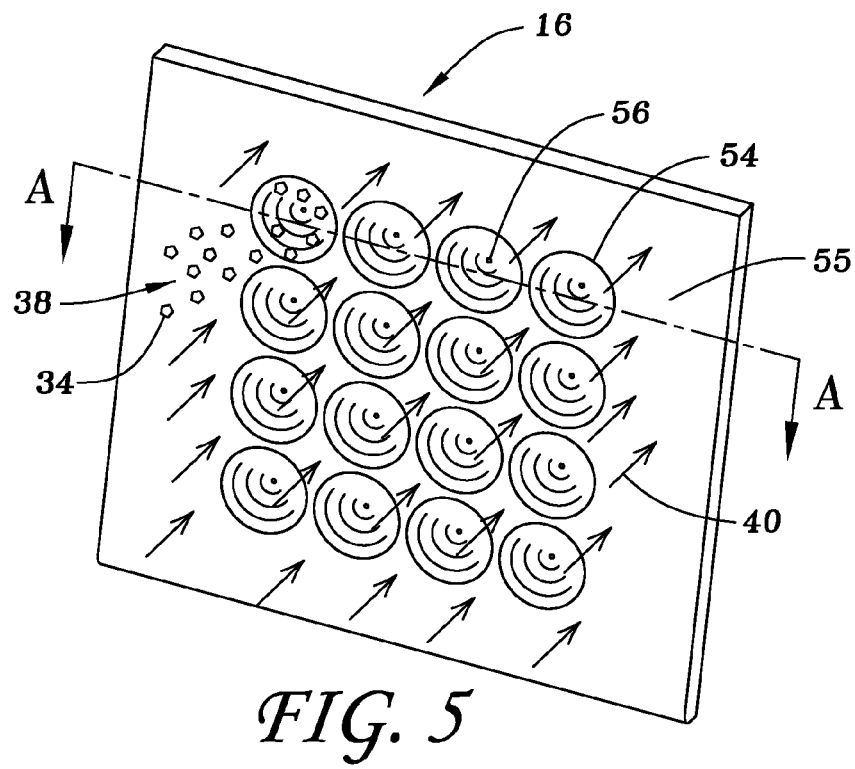
FIG. 5 depicts an air controller surface showing multiple air collection funnels leading to air inlets in gaseous fluid connection with the detection unit.

FIG. 5 depicts an air receiving surface of collector 16, particularly depicting cone-shaped funnels 54 to aid with directing air flow 40 to air inlet holes 56 of collector 16. The air receiving surface may have any surface configuration of inlet holes and/or funnels or otherwise configured openings to assist air collection. It should be noted that while flow-directing surfaces are preferable, they are not essential. A simple air inlet hole into collector would serve the purposes of the invention. Further, the number of inlets may be any number greater than or including one. The number of funnels/ducts/directional air devices may be any number greater than or including zero. The configuration shown may be altered to nonlinear patterns and may include any size and shape. However, it is beneficial to use a known pattern for the configuration of the collectors, since it may aid in determining exactly where the contaminant lies, therefore, for example, on small objects, allowing the contaminated section to be sanitized. This is easily comprehended. For example, if the collectors are placed, for instance, in a grid one centimeter apart and if a particular collector identifies contaminant, but the surrounding collectors do not, then it will be clear that the contaminant can be narrowed to at least the one centimeter radius surrounding the identifying collector.

Figure 6:
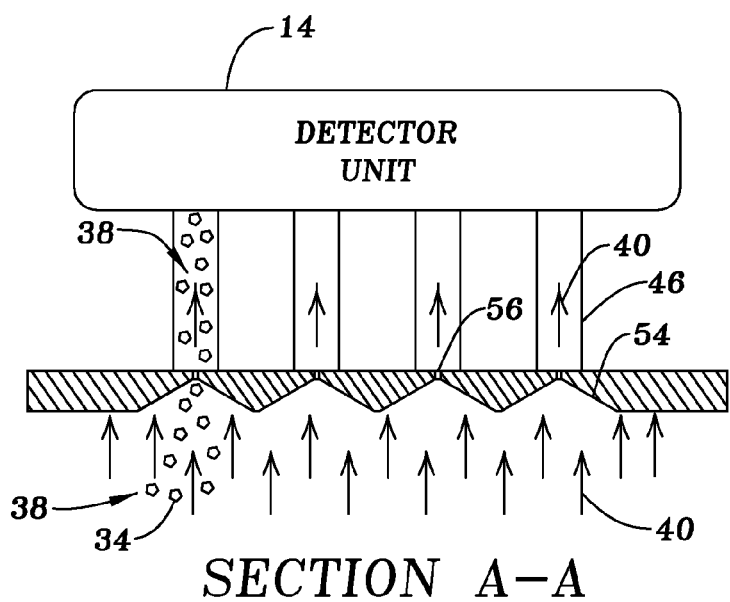
FIG. 6 depicts a cross-section of the center of a line of funnels as shown in FIG. 5, demonstrating contaminate particle/air stream flow through the air inlets and additionally depicting fluid connection to the detection unit.

FIG. 6 depicts a cross section of row of funnels 54 showing air flow 40 of a combined contaminant particle/air stream 38 with contaminant particles 34 through inlet holes 56 of funnels 54 and into tubing or ductwork 46 for transport of aerosol to detector 14 for analysis.

Figure 7:
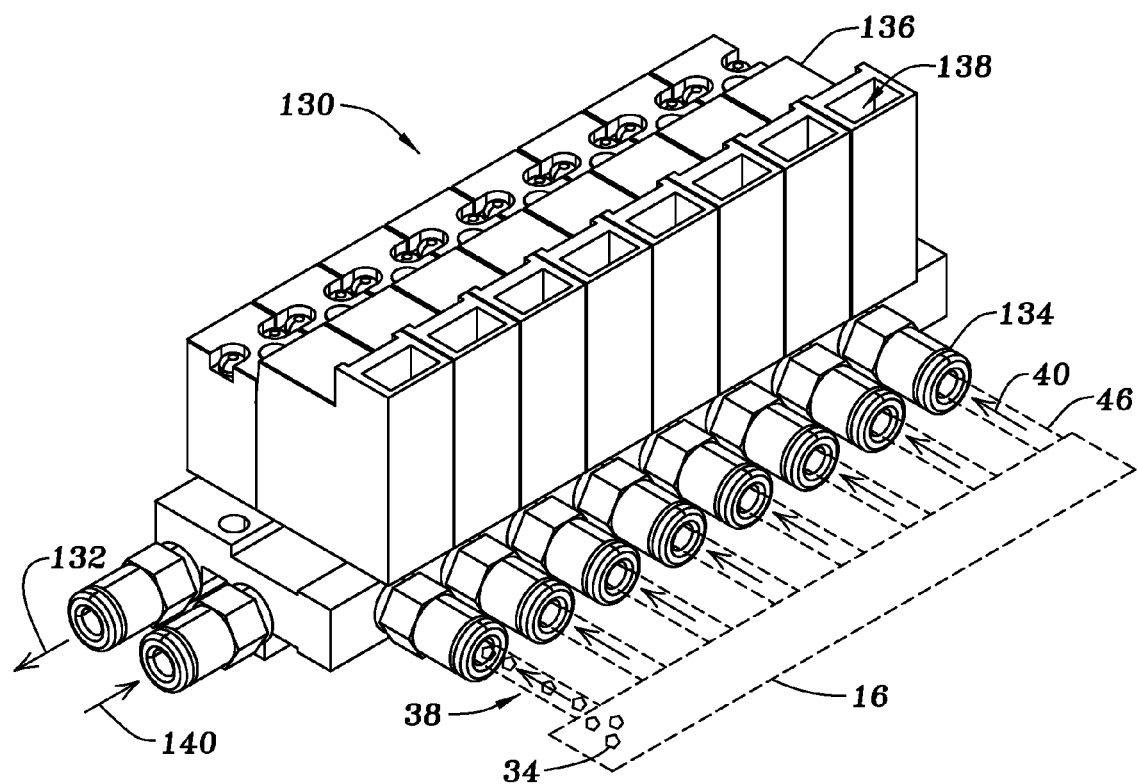
FIG. 7 depicts an air manifold for use in controlling air flow to each particular inlet.

FIG. 7 depicts an optional manifold assembly 130 to direct airflow with use of multiple collections of contaminant particle/air streams. If more than one manifold assembly is used, the assemblies would be tied together pneumatically as is well-known in the art to result in only one air flow output 132. Collected air 58 flows into manifold assembly 130 through tubing 46 from air inlet holes of collector 16. The tubings 46 are fittingly connected to fittings 134 of manifold assembly 130 and are directed into one or more manifold assemblies 130. The manifold assemblies contain solenoid valves 136 which can determine flow of the sample contaminant particle/air streams. The valves 136 may have electrical connections 138 thereto as known in the art for manual or computerized control of the opening and closing of the respective valves. The use of a manifold assembly for the invention may be particularly important for quality control assurances. A faulty intake may be determined by individual testing each intake through a particular funnel (or system). Additionally, optional air purge 140 would allow a reverse air flow through the system to purge blockages in the tubing which may occur through use or cleaning. Air flow 132 comprises the resultant air flow of the manifold.

Figure 8:
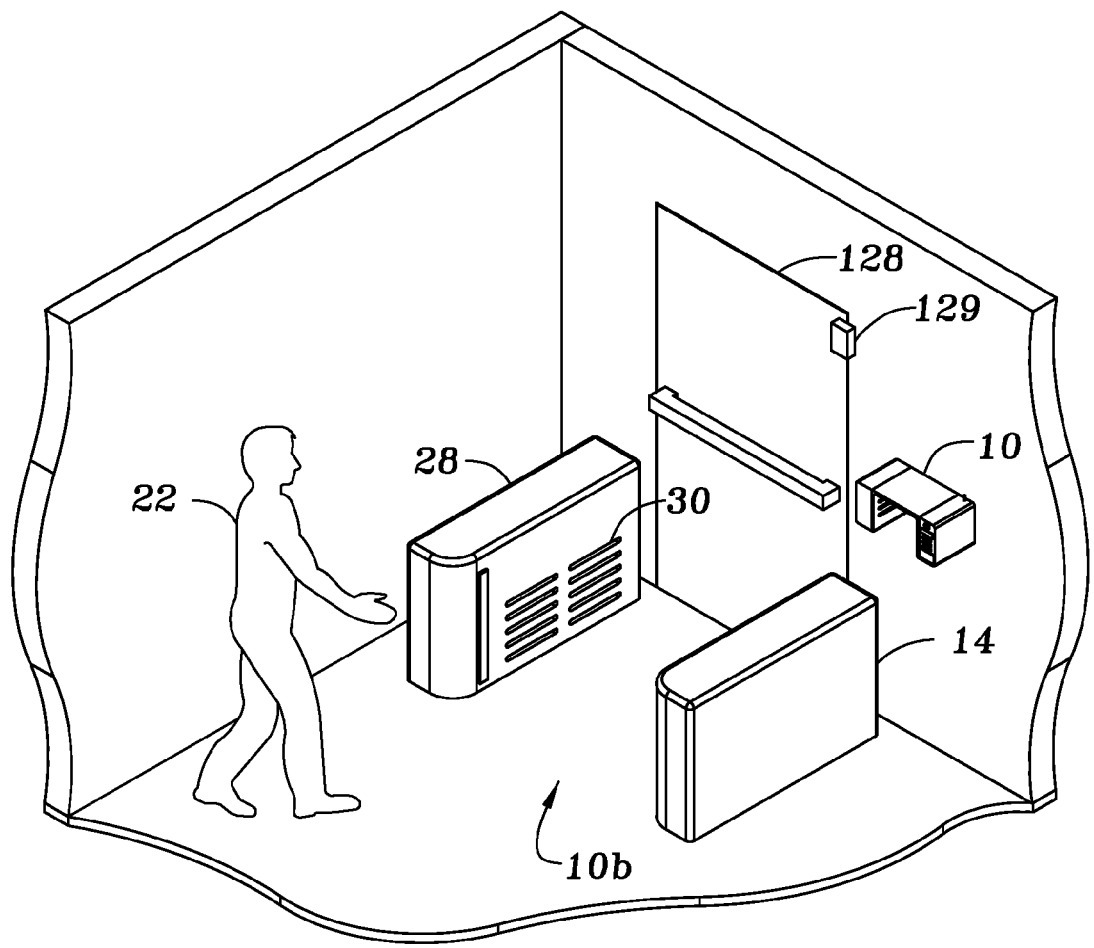
FIG. 8 is a perspective view of an embodiment of the invention which is particularly useful for clean rooms showing a floor unit for analysis of clean suits, a wall unit for hand/glove/small object detection and security devices which may prevent entry if a passing analysis does not occur.

It is envisioned that the apparatus of the present invention would be extremely useful not only for detecting contaminants on hands, such as after hand washing, but also for more stringent cleanliness requirements such as for a clean room or an operating room. As shown in FIG. 8, the apparatus of the invention can comprise a small unit 10 for detection of contaminants on hands, instruments, gloves, and the like, but can also be used in an alternate embodiment as, for example a floor unit, 10b wherein the object 22 to be examined comprises the body of the user or, for example, the feet of the user. As shown in FIG. 8, a user 22 can walk through a floor unit embodiment of the apparatus 10 of the invention in order for detection of contaminants to occur. Detection would occur in the same fashion as previously described herein, wherein either ambient air flow or air flow mechanically induced by air handler 28, sending an air stream through openings 30 and across user 22 to a collector in fluid connection with detector 14 would allow the detector to analysis aerosolized contaminant particles carried from the user by the air stream into the collector.

Preferably, in such situations where strict cleanliness requirements are needed, alternate security devices will be employed by the unit 10b and/or 10. For example, as depicted in FIG. 8, depending on the analysis of detector 14, the controller will send either a remote signal or a signal through conventional wiring to a security lock mechanism 129 on a door 128. If contaminants are found, then user 22 will not be able to pass through the door because lock mechanism 129 will not disengage.

Figure 10:
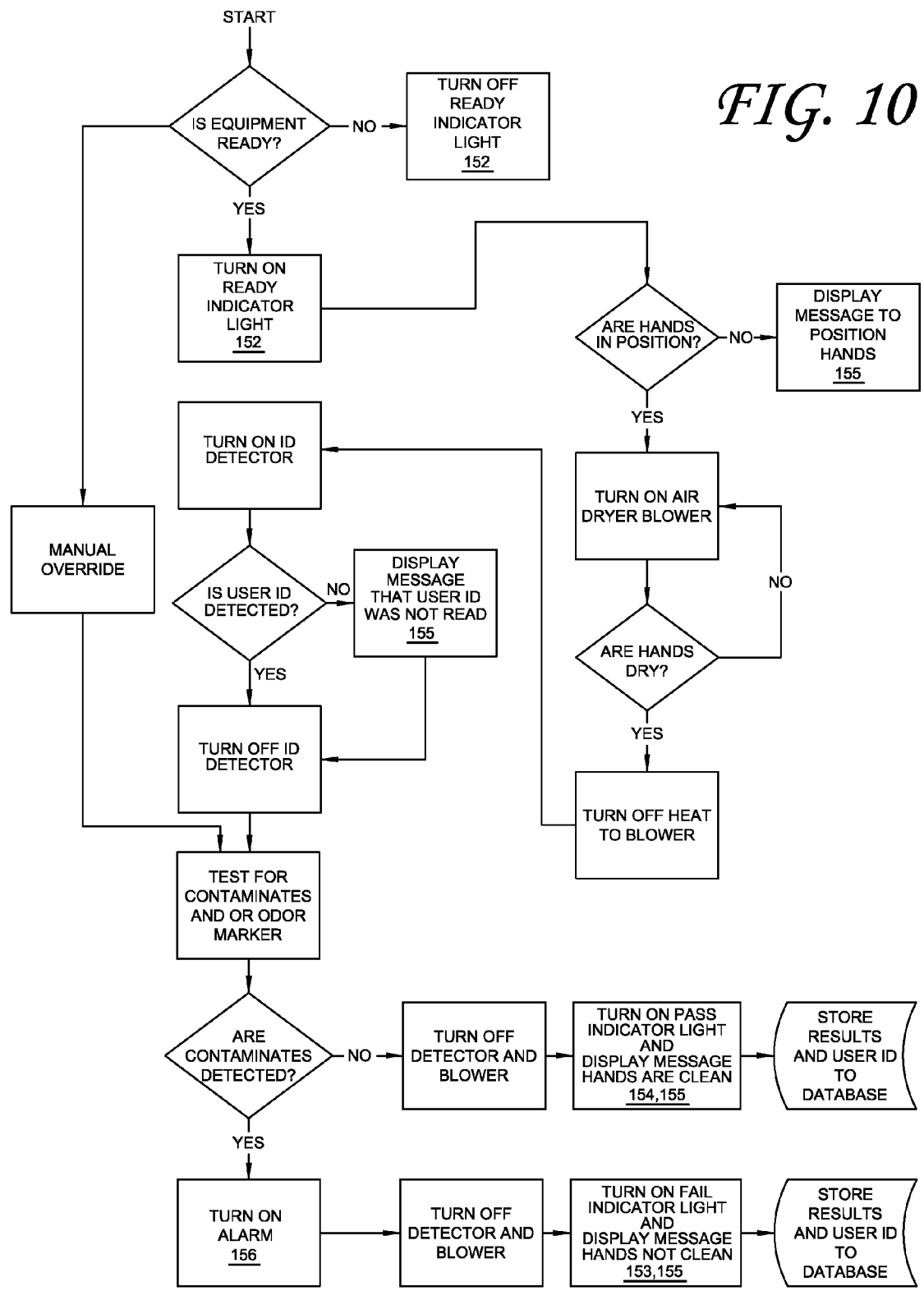
FIG. 10 is an example flow diagram for control processes of the controller unit of the invention.

The apparatus of the present invention optionally additionally comprises a controller unit, typically comprising a processor, as known in the art, which is capable of following pre-determined pathways based on input from the detector and extraneous optional sensors in electronic connection with the processor of the controller unit. Based on the outcome of the pre-determined pathways, the controller sends a signal, either by electronic connection or through, for example radio frequency transmissions/receivers or other means known in the art, to the corresponding unit, for instance the air handler to dictate, by pre-determined pathways what action to undertake, i.e., increase or decrease air flow. Any pathway may be programmed into the processor as desired. A preferred logic pathway for the processor is depicted in FIG. 10. The pathway indicated is for an inventive apparatus installed on a hand dryer device, which apparatus has internal sensors 34, identification tag reader and optional display modules 152, 153, 154, 155, 156 and RF transmission from antenna 157 as shown in FIG. 2.

The device of the invention could easily be modified to be used in a handheld or otherwise portable device, and/or in conjunction with already existing detectors such as fluorescence, metal, plastic or other types of contaminant detectors, in conjunction with restroom hand dryers or for any configuration necessary to accommodate industry. The essentials for the operation of the device are air flow over an object surface into collectors for analysis. It is envisioned that many differing configurations will be utilized and the embodiments depicted herein are offered to be illustrative but not limiting of the invention.

What is claimed is:

1. A method for detecting contaminants on objects comprising:
   placing at least one object in proximity to a detector for examination;
   collecting air surrounding the at least one object; and
   analyzing the collected air by use of the detector to determine the presence of aerosolized particles of the contaminants in the collected air utilizing an odor marker to identify the presence of an object.

2. The method of claim 1 comprising the additional step of utilizing an odor within a known object as an odor marker.

3. The method of claim 2 comprising the additional steps of providing exchangeable objects having known odor markers and maintaining a database or record of the analysis of odor markers to indicate use of particular exchangeable objects.

* * * * *